United States Patent [19]

Pawliszyn

[11] Patent Number: 5,237,824
[45] Date of Patent: Aug. 24, 1993

[54] APPARATUS AND METHOD FOR DELIVERING SUPERCRITICAL FLUID

[76] Inventor: Janusz B. Pawliszyn, 383 Dunvegan Dr., Waterloo, Canada, N2K 1W7

[21] Appl. No.: 613,784
[22] PCT Filed: Feb. 16, 1990
[86] PCT No.: PCT/CA90/00053
  § 371 Date: Oct. 12, 1990
  § 102(e) Date: Oct. 12, 1990
[87] PCT Pub. No.: WO90/09233
  PCT Pub. Date: Aug. 23, 1990
[51] Int. Cl.⁵ .................. F17C 7/102; B01J 14/00
[52] U.S. Cl. .................. 62/51.1; 62/47.1; 62/50.1; 62/50.2
[58] Field of Search .......... 62/45.1, 46.1, 47.1, 62/50.1, 50.4, 48.1, 51.1, 50.2

[56] References Cited

U.S. PATENT DOCUMENTS

| | | | |
|---|---|---|---|
| 2,482,778 | 9/1949 | Joerren | 62/46.1 |
| 3,062,017 | 11/1962 | Balcar et al. | 62/48.1 |
| 3,473,343 | 10/1969 | Chamberlain | 62/50.1 X |
| 3,827,246 | 8/1974 | Moen et al. | 62/47.1 |
| 3,925,048 | 12/1975 | Iung | 62/50.1 |
| 4,198,828 | 4/1980 | Mercier et al. | 62/50.1 |
| 4,854,128 | 8/1989 | Zeamer | 62/50.1 |
| 4,947,651 | 8/1990 | Neeser et al. | 62/50.4 |
| 4,961,325 | 10/1990 | Halvorson et al. | 62/50.1 X |
| 4,977,747 | 12/1990 | Frejaville et al. | 62/50.1 |
| 4,987,932 | 1/1991 | Pierson | 62/50.1 X |

FOREIGN PATENT DOCUMENTS 0116000 5/1988 Japan .................... 62/45.1

Primary Examiner—Henry A. Bennet
Assistant Examiner—Christopher B. Kilner
Attorney, Agent, or Firm—Daryl W. Schnurr

[57] ABSTRACT

A method and apparatus for delivering supercritical fluids uses one or two high pressure vessels. Each vessel is cooled below the critical temperature of the fluid while the vessel is being filled. The inlet is then closed and the vessel is heated to attain a predetermined pressure. The outlet of the vessel is then opened and supercritical fluid flows from the vessel for use in various processes such as extraction or chromatography. As the fluid flows from the high pressure vessel, the pressure is controlled by adjusting the temperature of the high pressure vessel. Usually, the temperature of the vessel will be increased as the supercritical fluid exits from the vessel. When two high pressure vessels are used, the vessels can be refilled on an alternating basis so that a continuous supply of supercritical fluid can be made available as long as it is required. The high pressure vessels can be two pieces of stainless steel tubing. The system is essentially maintenance free as there are virtually no moving parts. With previous delivery systems for high pressure fluids, high pressure pumps are used. These pumps are relatively expensive and can be subject to problems such as noise and leakage.

13 Claims, 6 Drawing Sheets

APPARATUS AND METHOD FOR DELIVERING SUPERCRITICAL FLUID

BACKGROUND OF THE INVENTION

1. Field of the Invention

This invention relates to a process and apparatus for delivering supercritical fluid and in particular to a process and apparatus that utilizes a high pressure vessel to deliver supercritical fluid.

2. Description of the Prior Art

Previously, supercritical fluid has been delivered through the use of high pressure pumps such as syringe pumps, membrane pumps and dual-piston pumps. Due to the high pressure requirements, these pumps are extremely expensive and are often prone to leaking, thereby reducing the efficiency. Also, these pumps can be unreliable for the delivery of fluids whose critical temperatures are below or slightly above room temperature. Since the supercritical fluid has a much lower viscosity than a "normal" liquid, the pump "leaks" if its head is above the critical temperature of the fluid. To solve this problem, it is necessary to cool off the heads, thereby increasing the complexity of the process. Further, the membrane and dual-piston pumps deliver fluid in pulses. In addition, all of the pumps are noisy. While syringe pumps can develop a high pressure quickly and do not produce a pulsating output, they have a small volume which may necessitate refilling the pump partway through an extraction process with which the pump is being used. Also, syringe pumps are more expensive than other pumps. In addition, the greater the pressure that a pump must produce, the greater the difficulty in controlling leakage and, generally, pumps are not used to produce a pressure greater than 10,000 psi. Pumps are subject to long term maintenance.

SUMMARY OF THE INVENTION

It is an object of the present invention to provide a process and apparatus for supercritical fluid delivery based on high pressure vessels where a continuous supply of supercritical fluid can be produced on a consistent basis.

A process for delivering supercritical fluid for various uses has a high pressure vessel with means to cool and means to heat said vessel. The vessel has an inlet and an outlet with control means to control the flow of fluid through said inlet and through said outlet. The inlet is connected to a pressurized fluid source and the process includes the steps of lowering the temperature of the vessel below the critical temperature of the fluid while opening the inlet to fill the vessel with fluid, closing the inlet, heating the vessel while monitoring the temperature and pressure to greatly increase the pressure until the desired pressure is attained, opening the outlet to deliver supercritical fluid from the vessel while continuously adjusting the temperature during the delivery of the fluid to control the pressure as desired.

An apparatus for continuously delivering supercritical fluid is characterized by two high pressure vessels, each vessel having an inlet and an outlet. The vessels are connected in parallel and the inlets of each vessel are connected to a pressurized fluid source. There are means to cool and means to heat each vessel with control means to cool, heat, fill and empty the two vessels independently.

DESCRIPTION OF A PREFERRED EMBODIMENT

Figure 1:
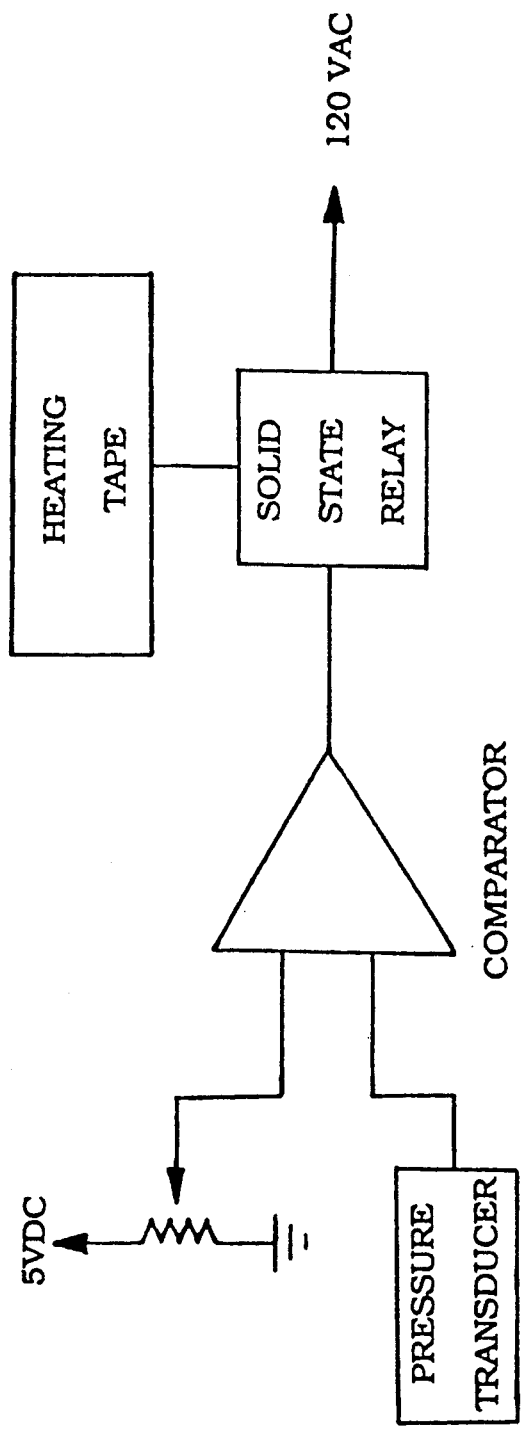
FIG. 1 is a block diagram of an electronic circuit for controlling pressure in an extraction system.

In FIG. 1, there is shown an electronic circuit for controlling the pressure in an extraction system with which the supercritical fluid delivery system of the present invention is used. The pressure is first set by adjusting the position of the variable resistor. When the output voltage from the pressure transducer exceeds a preset value, the state of the comparator output changes, switching off the supply of the power to the heating tape or heater. The switching on and off is done with the help of a solid state relay (Model EOM-1DA42-3/32, Potter and Broomfield, a trade mark). A similar electronic circuit (not shown) is used to control temperature in the extraction vessel. More sophisticated control of the extraction conditions can be performed with the held of a PC AT (a trade mark) compatible computer equipped with an IBM-DACA (a trade mark) acquisition board and ASYST (a trade mark) software. Control of the extraction conditions can be performed with a proportional-integral-derivative (PID) method using software enabling the continuous acquisition of pressures and temperature readings and switching on/-off of the power supply to the heater. Other conventional PID controllers are available to control pressure.

Figure 2:
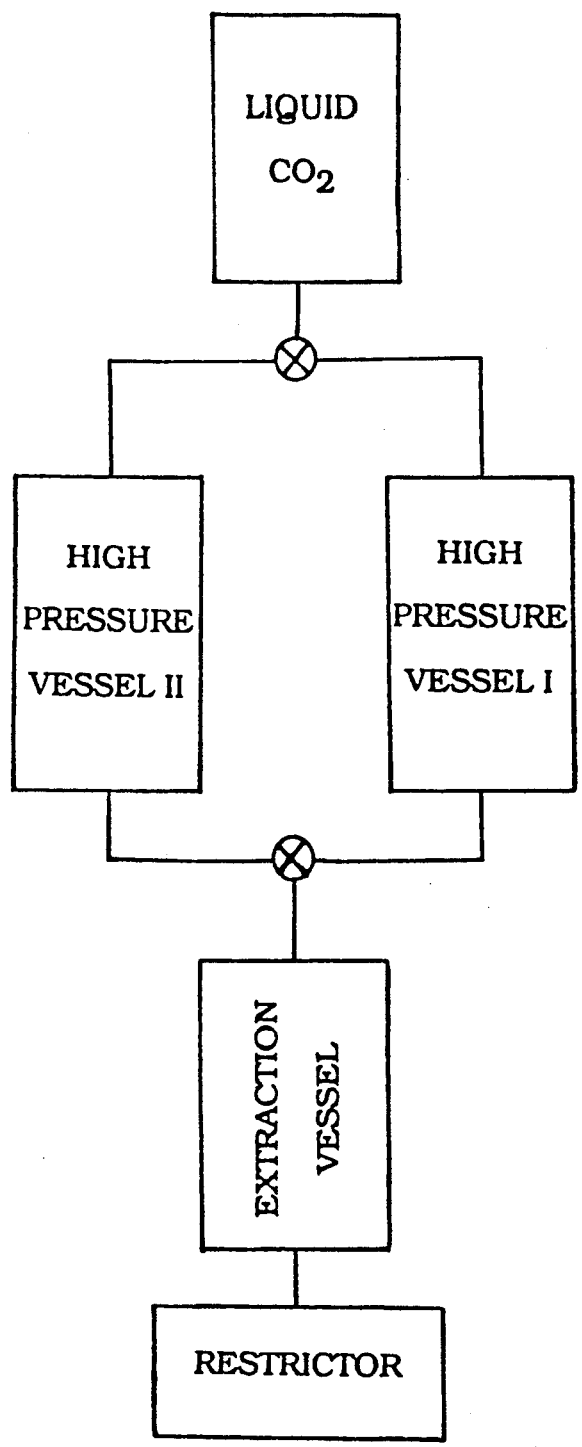
FIG. 2 is a block diagram of an apparatus, having two high pressure vessels, for delivering supercritical fluid.

In FIG. 2, there is shown a supercritical fluid delivery system having two high pressure vessels, each vessel having an inlet and outlet, said vessels being connected in parallel. The inlets of each vessel are connected to a pressurized fluid source, for example, liquid carbon dioxide. There are means to cool and means to heat each vessel, with control means to cool, heat, fill and empty the two vessels independently. The outlets are connected to an extraction vessel, which in turn is connected to a restrictor. The extraction vessel is one use of the supercritical fluid delivered by the present system. Various other uses are available, for example, chromatography. The three valves shown on the inlet side of the vessels could be replaced by one three-way valve. The three valves on the inlet to the vessels can also be controlled by a single electronically controlled ten port valve equipped with a speedup kit. This ten port valve will change positions on command from a computer where a computer is used to control the system.

The extraction vessel is a commercially available three column (VALCO, a trade mark, Instrument Company Inc.) equipped with a twenty $\mu$m inside diameter fused silica capillary which works as a restrictor. The heating of this vessel is done by a heating tape. A gas chromatograph-mass spectrometer (Model HP5890/5970, Hewlett Packard, a trade mark) was used to analyze extracted mixtures.

Figure 3:
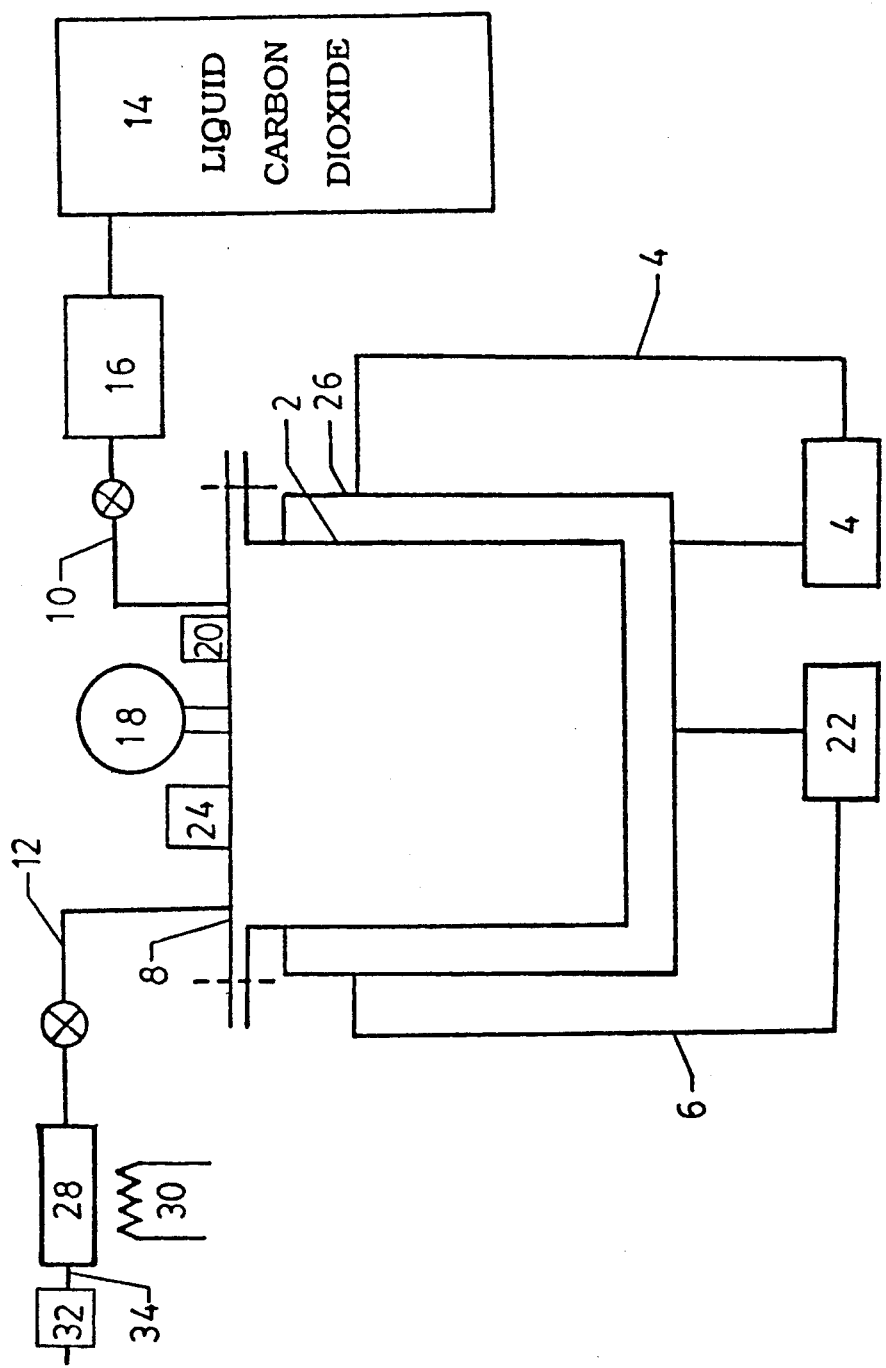
FIG. 3 is a schematic drawing of a system for delivering supercritical fluid having a single high pressure vessel.

In FIG. 3, there is shown a system, for delivering supercritical fluid, having a high pressure vessel 2 with means 4 to cool the vessel and means 6 to heat the vessel. The vessel 2 has a removable cover 8 with an inlet 10 and an outlet 12. The inlet 10 is connected to a pressurized fluid source 14, for example, carbon dioxide. An activated carbon trap 16 in the inlet line 10 assists in purifying the carbon dioxide. A pressure gauge 18 monitors the pressure within the vessel 2. Pressure within the vessel is regulated electronically by using a pressure transducer 20 which is connected to a thermostat 22 on the heating means 6, said thermostat controlling the temperature of the vessel 2. A pressure relief valve 24 on the vessel 2 ensures that the vessel will not explode, the valve 24 being set at a much lesser pressure than the vessel 2 cap withstand. A heating/cooling jacket 26 surrounds the vessel and may be in the form of 0.25 inch inside diameter copper tubing that is welded to an outside surface of the vessel. Ice water or expanded carbon dioxide or other fluid can be passed through the tubing to cool the vessel. The vessel can be heated using heating tape. The outlet 12 is connected to an extraction vessel 28 which is equipped with an electrical heater 30 and has a restrictor 32 located at its outlet 34. While the fluid outlet is shown in FIG. 3 to be connected to an extraction vessel, that is but one example of a type of use for the supercritical fluid. Various other uses will be readily apparent to those skilled in the art. One other suggested use for the supercritical fluid is chromatography.

The vessel can be made of any suitable material, for example, stainless steel. All of the high pressure vessels used in the present invention were constructed to withstand pressures in excess of 20,000 psi while the pressure relief valve contains disks which rupture at 7,000 psi. The temperature in both the high pressure vessel 2 and the extraction vessel 28 is monitored using thermisters.

In operation, the supercritical fluid delivery system described in FIG. 3 is activated by lowering the temperature of the vessel 2 below the critical temperature of the fluid while opening the inlet 10 to fill the vessel 2 with fluid. The critical temperature for carbon dioxide is 32° C. The temperature is lowered by passing coolant through the cooling means 4. When the vessel has been filled with liquid fluid from a high pressure cylinder or fluid source 14, the inlet 10 is closed and the vessel is heated through the heating means 6 by monitoring the temperature and pressure to greatly increase the pressure until a desired pressure is attained. The outlet 12 is then opened while continuously adjusting the temperature during delivery of the fluid to control the pressure as desired. If the temperature is not adjusted, the pressure will slowly drop when the outlet 12 is opened and the vessel begins to empty. Pressure can be controlled at a constant level when the outlet 12 is opened by raising the temperature of the high pressure vessel. Further, pressure can be increased, if desired, when the outlet 12 is open, by increasing the temperature of the high pressure vessel 2 at a higher rate. Pressures can be regulated by using a simple electronic circuit as presented in FIG. 1 or by a more precise proportional-integral-derivative (PID) method enabling the continuous acquisition of pressures and temperature readings and switching the power supply to the heating means 6 on and off, as required. Conventional PID controllers can be used to control pressure. The amount of fluid which can be used in an extraction process is determined by the volume of the high pressure vessel and its maximum temperature. As an example, in one embodiment of the system of FIG. 3, the temperature limit is 140° C. At this temperature, when carbon dioxide is used as the fluid, the density of the carbon dioxide at an extraction pressure of 300 atm. is approximately 0.5 g./ml. Depending on the initial temperature, 30% to 50% of carbon dioxide was able to be used.

Figure 4:
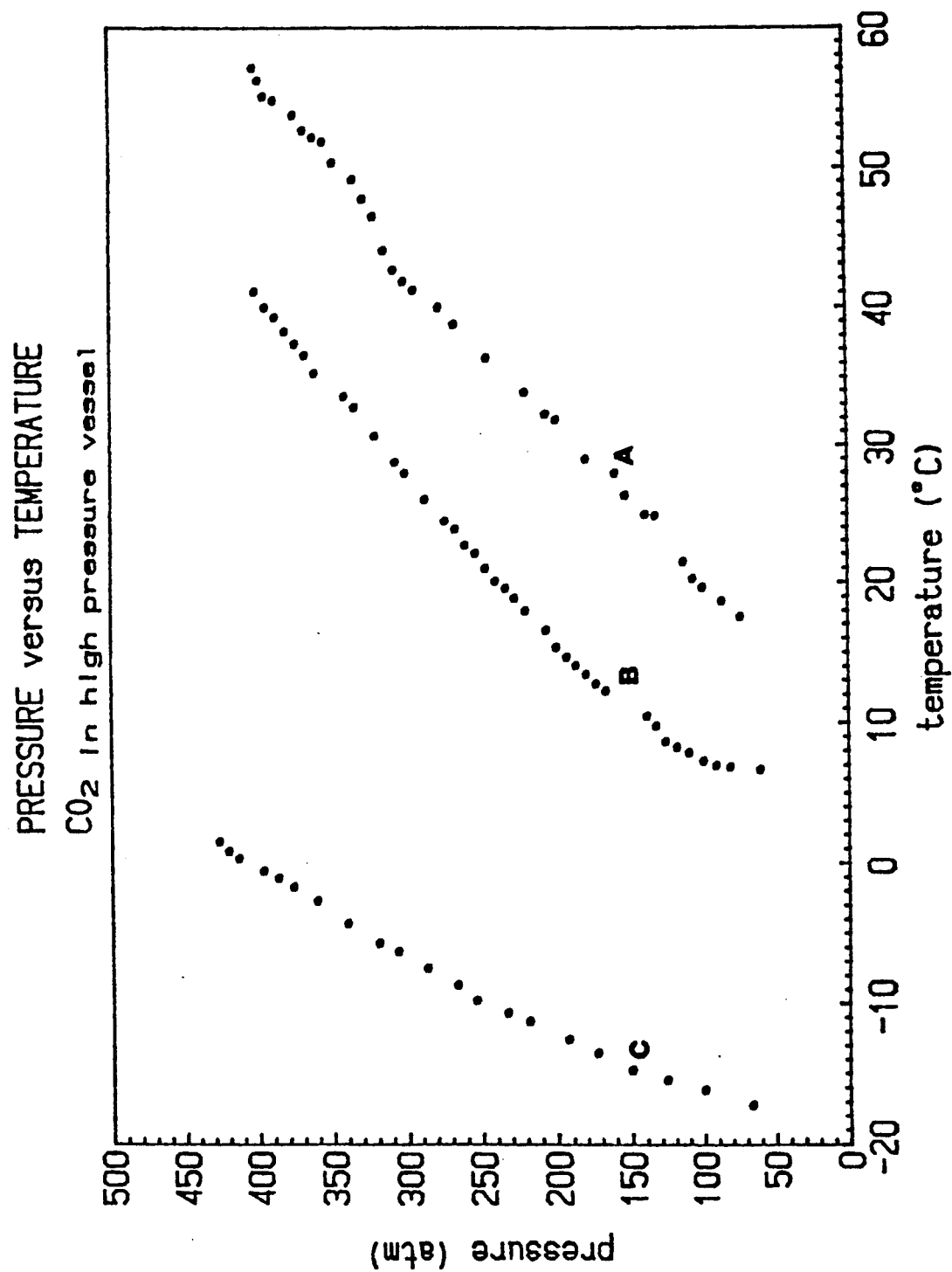
FIG. 4 is a graph of the change of pressure with temperature in a high pressure vessel.

In FIG. 4, there is a graph showing a typical relationship between the pressure of carbon dioxide contained in a high pressure vessel and its temperature. As expected, the pressure increases as the temperature increases. The three different curves shown correspond to different initial temperatures of the high pressure vessel during which the device was filled with liquid carbon dioxide. If the vessel is charged at temperatures close to room conditions (i.e. approximately 20° C.) then the curve labelled A is applicable and the liquid must be heated to approximately 45° C. to supply fluid at extraction conditions which are usually carried out at approximately 300 atm. Similarly, referring to the B curve, when the initial temperature is approximately 7° C. while the vessel is being filled, the temperature must be increased to approximately 25° C. in order to increase the pressure to approximately 300 atm. On the other hand as shown in the curve labelled C, by initially cooling the vessel below −15° C. while the vessel is being filled, the same pressure of 300 atm. and even higher values can be achieved by increasing the temperature to a level of less than 0° C. The density of liquid carbon dioxide is approximately 0.8 g./ml at room temperature and approximately 1.0 g./ml at −15° C. The amount of carbon dioxide in the vessel when the vessel is initially cooled to −15° C. while it is being filled is approximately 30% more than the carbon dioxide in the same size container when the initial temperature is close to room conditions. Therefore, initially cooling the high pressure vessel to a lower temperature will result in a larger amount of carbon dioxide being available for use in an extraction process. Unfortunately, it is more difficult to control temperatures below ambient conditions. Accidental increase of the temperature of the vessel associated with curve C of FIG. 4 might cause the pressure to increase beyond the capabilities of the pressure relief valve.

It has been found that a 200 ml high pressure vessel can supply approximately 50 l of carbon dioxide gas at ambient pressure. In a continuous supercritical fluid extraction process with a 20 μm restrictor, the carbon dioxide flow rate is approximately 150 ml a minute. Therefore, a 200 ml vessel can deliver supercritical fluid continuously for approximately five hours. A single supercritical extraction process normally takes only a few minutes and therefore there is plenty of fluid to complete several extraction processes.

If more fluid is required on a continuous basis, the size of the high pressure vessel can be increased or, preferably, a supercritical fluid delivery system similar to that described in FIG. 2 can be utilized. In that system, there are two high pressure vessels connected in parallel. While the first high pressure vessel is being used to supply fluid to an extraction vessel, the second high pressure vessel can be filled with fluid. Once the second vessel has been filled with fluid, the pressure in the second vessel can be increased by increasing the temperature of the second vessel to attain the required extraction pressure. As the first vessel becomes empty, a predetermined maximum temperature will be attained for the first vessel. The outlet from the first vessel will then be closed and, simultaneously, the outlet from the second vessel will be opened. As fluid is supplied from the second vessel, the temperature of the second vessel will be increased. At the same time, the first vessel will be cooled, refilled and heated to achieve the required extraction pressure. This process can be repeated as long as a continuous supply of supercritical fluid is required.

In order to ensure that there is no detectable drop in pressure in the extraction system during the switching from one high pressure vessel to another high pressure vessel, a high speed valve can be utilized to close the outlet from one vessel and open the outlet from the other vessel simultaneously. It has been found that when the system of FIG. 2 is designed with one valve controlling both outlets and the valve has a switching time of approximately 100 microseconds that no detectible drop in pressure occurs in the extraction system. Where separate valves are used for the outlet of each vessel and where the valves are not high speed valves, to ensure that there is no detectable pressure drop in the extraction system during switching, the outlet from the most recently filled vessel should be opened first before closing the outlet from the nearly empty vessel.

The density of the fluid in the extraction vessel and therefore its solubility or extraction properties are independent from the density of the fluid that exists in the high pressure vessel. Only the extraction pressure is determined by the conditions in the high pressure vessel. The extraction temperature which determines density of the fluid is regulated independently by using a heater on the extraction vessel itself. Thus, the system of the present invention can be used to supply supercritical fluid to an extraction process which allows much better control of extraction conditions than previous systems that are used in batch extractors where the supercritical fluid is poured directly into the extraction vessel. The gas cylinder supplying the fluid to the high pressure vessel contains high purity grade fluid. The density of the fluid increases significantly with a decrease in temperature close to the critical pressure.

Figure 5:
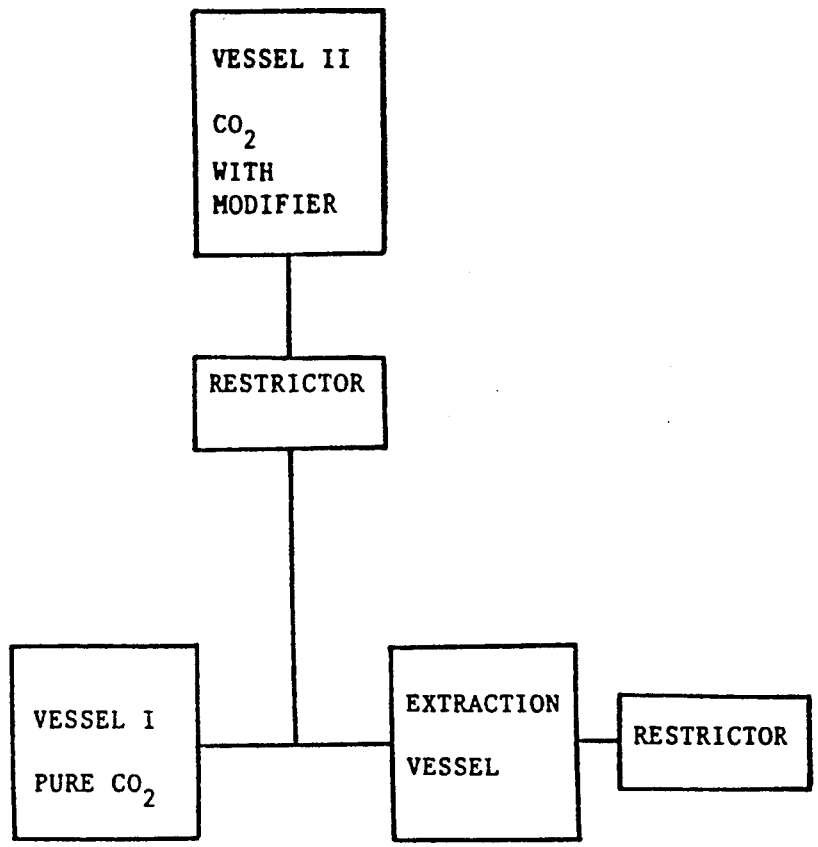
FIG. 5 is a block diagram of a supercritical fluid delivery system having two high pressure vessels, one vessel containing a modifier.

In FIG. 5, there is shown a further embodiment of the process and apparatus of the present invention where a supercritical fluid delivery system has two high pressure vessels, one vessel being filled with pure fluid and the other being filled with the fluid and a modifier. The first vessel which contains the pure carbon dioxide has an outlet connected directly to the extraction vessel. The second vessel contains a high concentration of modifier and has an outlet connected to the extraction system through a restrictor. The differential pressure which exists between the second vessel and the extraction system determines the flow magnitude of the modifier from the second vessel and therefore the composition of the extraction fluid. Alternatively, a modifier could simply be added to a supercritical fluid delivery system having only one high pressure vessel by adding the modifier directly to that vessel while it is being filled with fluid.

Most supercritical fluid extractions of environmental samples have presently been performed in the dynamic (leaching) mode. In these methods, the organic compounds of the sample are continuously leached with supercritical fluid and then transferred and deposited by flowing and expending the fluid. However, fractionation of various components of the mixtures can be achieved by using the static approach which will allow for equilibrium to be reached. In this situation, significant partitioning based on solubilities of various components in the supercritical mixture can be achieved. Also, matrix effects can be exploited to further fractionate the components. The system of the present invention provides significant advantages compared to delivery systems using pumps in this particular application. A continuous flow of solvent is not required to maintain the pressure in the system. Also, the highly controlled pressure can be supplied through extractors in static configurations by connecting them directly to the high pressure vessel.

As an example, the system described in FIG. 5 was used to extract organic components from municipal incinerator fly ash and the mixture was analyzed for dioxins and dibenzofurans. The procedure involved first the removal of hydrocarbons at low pressures (2,000 psi) with pure supercritical carbon dioxide and then at high pressure (300 atm.) with 10% benzene to extract chlorinated aromatic hydrocarbons. The benzene was added as a modifier to the carbon dioxide in the second vessel. In Table 1, there are shown the results obtained for a prior art procedure involving soxhlet liquid extraction when compared to supercritical fluid extraction in accordance with the present invention. A separate category is set out in the Table for tetrachlorodibenzo dioxins as the most toxic component 2, 3, 7, 8-tetrachlorodibenzo-p-dioxin is a member of this subgroup. It can be seen from the Table that after two hours, the soxhlet method removes less than 50% of the chlorinated dioxins and dibenzofurans from fly ash as indicated by the twenty hour procedure which is required for complete extraction. By comparison, the supercritical fluid extraction process of the present invention achieves the complete isolation of these toxins from the fly ash matrix in two hours. The soxhlet extraction shown in Table 1 was performed using benzene as the solvent. The supercritical fluid method of the present invention consisted of two steps. Initially, low molecular weight hydrocarbons were removed at 150 atm. in 40° C. with pure carbon dioxide. Then, chlorinated aromatics were isolated at 300 atm. in 40° C. with 10% benzene contained in the carbon dioxide fluid, the benzene being a modifier.

TABLE I

ANALYSIS OF MUNICIPAL INCINERATOR FLY ASH BY SOXHLET AND SUPERCRITICAL FLUID EXTRACTION FOLLOWED BY GC/MS

| GROUP OF COMPOUNDS | | CONCENTRATION IN PPB | | |
|---|---|---|---|---|
| | | Soxhlet 20h | Soxhlet 2h | Supercritical Fluid Extraction 2h |
| POLYCHLORINATED DIBENZODIOXINS | TOTAL | 514 ± 10 | 229 | 486 ± 7 |
| | Tetrachloro-dibenzodioxins | 31 ± 6 | 11 | 35 ± 2 |
| TOTAL OF | | 180 ± 7 | 89 | 193 ± 8 |

TABLE I-continued

ANALYSIS OF MUNICIPAL INCINERATOR FLY ASH BY SOXHLET AND SUPERCRITICAL FLUID EXTRACTION FOLLOWED BY GC/MS

| GROUP OF COMPOUNDS | CONCENTRATION IN PPB | | |
|---|---|---|---|
| | Soxhlet 20h | Soxhlet 2h | Supercritical Fluid Extraction 2h |
| POLYCHLORINATED DIBENZOFURANS | | | |

As another example, poor extraction capabilities of carbon dioxide toward dioxins and furans, as shown in Table II, can be used effectively to clean up fly ash prior to extraction of the toxins. This carbon dioxide extraction step removes weakly bonded organic molecules in the matrix. This step can be followed by removal of compounds of interest with nitrous oxide. It has been found that extraction with $CO_2$ removes chlorinated compounds, which elute early. They are likely to be lower molecular weight or less polar compounds compared to the polychlorinated dioxins and furans. Extractions of acid etched fly ash with $CO_2$ and untreated fly ash with $N_2O$ give results similar to those corresponding to soxhlet extraction with benzene. It has also been found that the $N_2O$ chromatogram is significantly cleaner in the low retention time region since extraction with this fluid is preceded with $CO_2$ extraction at 325 atm. This two step extraction process can be used commercially to clean up fly ash.

Figure 6:
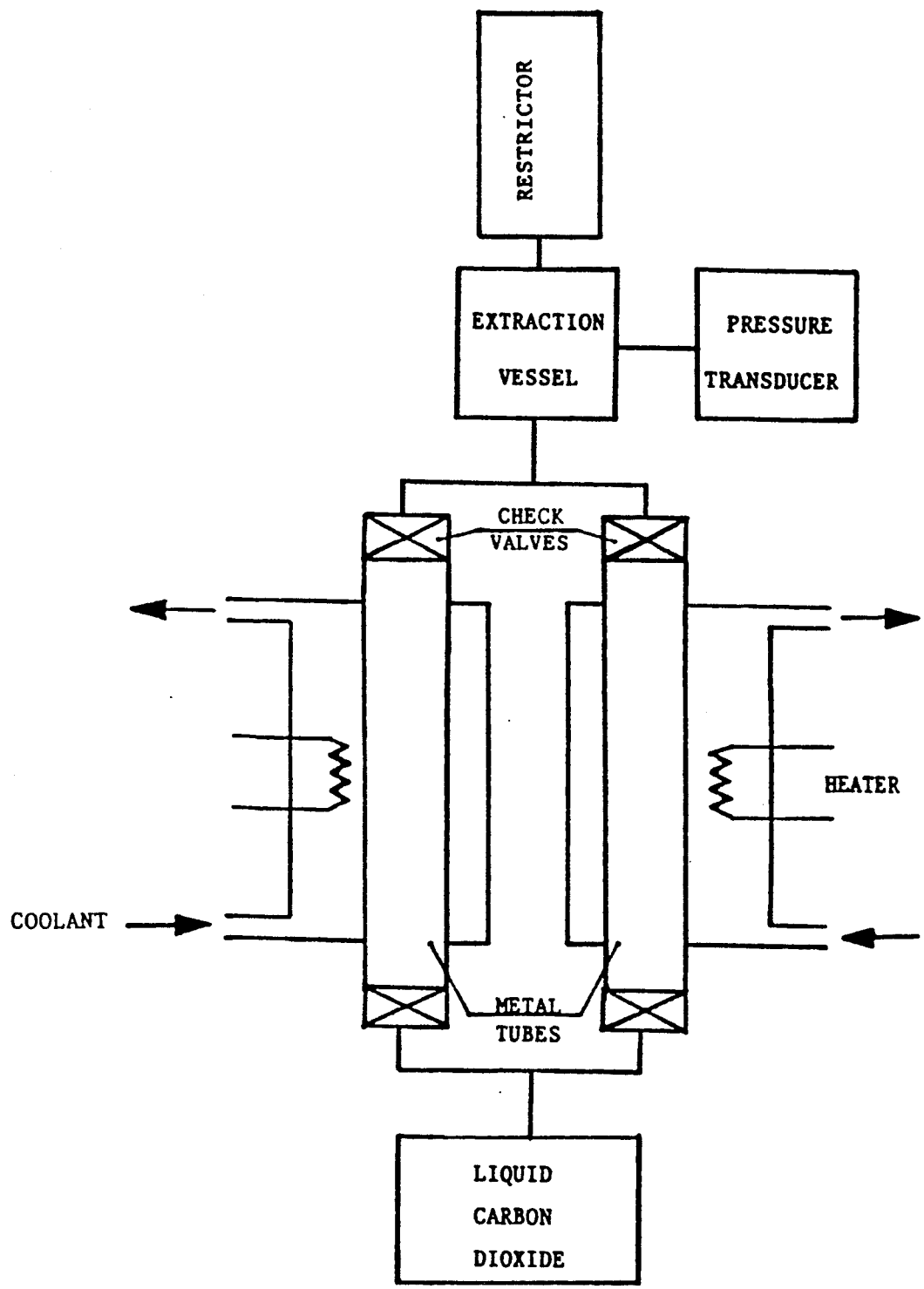
FIG. 6 is a schematic diagram of a supercritical fluid delivery system having two high pressure vessels with outlets controlled by check valves.

In FIG. 6, there is shown a supercritical fluid delivery system that is very similar to the system shown in FIG. 2 except that check valves are utilized on the outlets of the first and second high pressure vessels. Also, the high pressure vessels themselves are constructed from stainless steel tubing. The check valves operate so that a first check valve will automatically open and a second check valve will automatically close when the pressure on the first check valve exceeds the pressure on the second check valve. When the pressure on the second check valve exceeds the pressure on the first check valve, the opposite result will occur.

traction process for approximately five hours. Of course, small volume tubing can be filled with fluid in a few minutes but it will empty in a shorter time period as well.

While only carbon dioxide and carbon dioxide as modified by benzene were discussed as supercritical fluids in the present application, numerous other suitable supercritical fluids and modifiers will be readily apparent to those skilled in the art. For example, methanol, hexane, dichloromethane and toluene can be used as modifiers or as supercritical fluids. In addition, nitrous oxide, pentane, butane, ammonia and even water are some other supercritical fluids that can be used in extraction processes. Nitrous oxide is as commonly used as carbon dioxide.

The system described in FIG. 6 allows for the miniaturization of the system by replacing the high pressure vessels with pieces of stainless steel tubing. Obviously, miniaturization limits the amount of supercritical fluid that will be available for extraction. However, if a continuous supply of supercritical fluid is necessary in relatively low volume amounts, the system can be made from two pieces of tubing connected in parallel as shown in FIG. 6 and operated in the same manner as the system of FIG. 2. When the system is miniaturized, a silicon chip can be used for heating and cooling.

The supercritical fluid delivery system can also be used for supercritical fluid chromatography. The extraction vessel is simply replaced by a capillary column. If flow control rather than pressure control is required, a flow transducer can be coupled directly with the high

TABLE II

Extraction Data of Polychlorinated Dibenzo-p-dioxins and Dibenzofurans from Municipal Incinerator Fly Ash Using Supercritical Fluid Extraction with Different Fluids at 400 atm[a]

| PCDD / PCDF | $CO_2$ 40° C. 2 h $\bar{x}$ | $CO_2$ + 10% benzene 60° C. 2 h | | $CO_2$ + 10% toluene 60° C. 2 h $\bar{x}$ | $CO_2$ acid-treated fly ash 40° C. | | $N_2O$ 40° C. 2 h | |
|---|---|---|---|---|---|---|---|---|
| | | $\bar{x}$ | s, % | | $\bar{x}$ | s, % | $\bar{x}$ | s, % |
| T4CDD | | 117 | 12 | 49 | 96 | 25 | 98 | 7 |
| P5CDD | | 96 | 13 | 54 | 90 | 4 | 83 | 8 |
| H6CDD | | 96 | 11 | 57 | 87 | 8 | 81 | 2 |
| H7CDD | | 78 | 7 | 91 | 83 | 3 | 74 | 1 |
| O8CDD | | 75 | 6 | 35 | 75 | 17 | 81 | 6 |
| T4CDF | 19 | 88 | 5 | 53 | 92 | 5 | 83 | 5 |
| P5CDF | 9 | 97 | 5 | 48 | 114 | 5 | 87 | 1 |
| H6CDF | 19 | 97 | 5 | 54 | 111 | 7 | 88 | 4 |
| H7CDF | | 79 | 48 | 65 | 100 | 17 | 89 | 4 |
| O8CDF | | 94 | 6 | 16 | 65 | 18 | 91 | 6 |

[a]The units are in percent of extraction compared to 20 h of Soxhlet extraction. Estimated standard deviation s is expressed in percent of $\bar{x}$.

It has been found that the refilling process for a high pressure vessel having a volume of approximately 200 ml takes approximately twenty-five minutes. Therefore, there is more than sufficient time to refill the high pressure vessels on an alternating basis when the delivery system has two of such vessels. As previously stated, once a 200 ml vessel has been filled, it will be able to provide fluid for a typical continuous supercritical expressure vessel heater. The system has virtually no moving parts and is essentially maintenance free. Substantial cost savings can be achieved over systems that utilize pumps.

What I claim as my invention is:

1. A process for delivering supercritical fluid for various uses has a first high pressure vessel with means to cool and means to heat said vessel, said vessel having an inlet and outlet with control means to control the flow of fluid through said inlet and through said outlet, said inlet being connected to a pressurized fluid source, said process being characterized by lowering the temperature of said vessel below the critical temperature of the fluid while opening the inlet to fill the vessel with the fluid, closing the inlet, heating the vessel while monitoring the temperature and pressure to greatly increase the pressure until a desired pressure is attained, opening the outlet to deliver supercritical fluid from the vessel while continuously adjusting the temperature during delivery of the fluid to control the pressure as desired.

2. A process as claimed in claim 1 wherein, while the vessel is delivering supercritical fluid, controlling the temperature by increasing it to maintain a substantially constant pressure.

3. A process as claimed in claim 1 wherein while the vessel is delivering supercritical fluid controlling the temperature by increasing it rapidly to cause the pressure to increase at a predetermined rate.

4. A process as claimed in claim 1 wherein there is a second high pressure vessel connected in parallel to said first vessel with means to cool and means to heat said second vessel, said second vessel having an inlet and an outlet, said control means being adapted to control the flow of fluid through said inlet and through said outlet of said second vessel, the inlet of said second outlet being connected to a pressurized fluid source, said control means controlling the cooling, heating, inlet and outlet of each vessel independently, said process being characterized by, while said first vessel is delivering supercritical fluid, lowering the temperature of the second vessel below the critical temperature of the fluid while opening the inlet to the second vessel to fill the second vessel with fluid, closing the inlet to the second vessel, heating the second vessel while monitoring the temperature and pressure to greatly increase the pressure to the desired level, waiting for the vessel, immediately closing the outlet of the first vessel when said first vessel is substantially empty and opening the outlet of the second vessel to deliver supercritical fluid from the second vessel while continuously adjusting the temperature of the second vessel during delivery of the fluid to control the pressure as desired until the second vessel is substantially empty of fluid, repeating the process to recharge the first vessel with supercritical fluid and ultimately the second vessel, as desired.

5. A process as claimed in claim 4 wherein while the vessels are delivering supercritical fluid, adjusting the temperature by increasing it to maintain a substantially constant pressure.

6. A process as claimed in claim 4 wherein while the vessels are delivering supercritical fluid, adjusting the temperature by increasing it rapidly to cause the pressure to increase at a predetermined rate.

7. A process as claimed in claim 1 wherein there is a second high pressure vessel connected in parallel to said first vessel with means to cool and means to heat said second vessel, said second vessel having an inlet and an outlet, said control means being adapted to control the flow of fluid through said inlet and through said outlet of said second vessel, the inlet of said second vessel being connected to a pressurized fluid source, said control means controlling the cooling, heating, inlet and outlet of each vessel independently, there being a restrictor connected in the outlet of the second vessel, said second vessel containing a modifier, said process being characterized by adding a modifier to said second vessel, lowering the temperature of the second vessel below the critical temperature of the fluid while opening the inlet to the second vessel to fill the second vessel with fluid and modifier, closing the inlet to the second vessel, heating the second vessel while monitoring the temperature and pressure to greatly increase the pressure to the desired level, having both the first vessel and second vessel charged with supercritical fluid and opening the outlets of said first vessel and said second vessel independently as required to deliver supercritical fluid from the first vessel or supercritical fluid and modifier from the second vessel while continuously adjusting temperature of the first and second vessel during delivery of the fluid to control the pressure as desired until each vessel is substantially empty of fluid.

8. An apparatus for continuously delivering supercritical fluid, said apparatus being characterized by two high pressure vessels, each vessel having an inlet and an outlet, said vessels being connected in parallel, said inlets of each vessel being connected to a pressurized fluid source, there being means to cool and means to heat each vessel, with control means to cool, heat, fill and empty the two vessels independently.

9. An apparatus as claimed in claim 8 wherein the outlets on each vessel are check valves that are connected so that a first check valve will close and a second check valve will open as soon as the pressure on the second check valve exceeds the pressure on the first check valve and subsequently the second check valve will close and the first check valve will open as soon as the pressure on the first check valve exceeds the pressure on the second check valve.

10. An apparatus as claimed in any one of claims 8 or 9 wherein the vessels are constructed from stainless steel tubing.

11. An apparatus as claimed in any one of claims 8, 9 or 10 wherein the supercritical fluid is selected from the group of carbon dioxide and nitrous oxide.

12. An apparatus as claimed in any one of claims 8, 9 or 10 wherein said means to cool is capable of cooling each high pressure vessel well below the critical temperature of the fluid so that, when the inlet to that vessel is closed and the vessel is heated until a predetermined pressure is attained, the temperature of the fluid at that point in time is much less than its supercritical temperature.

13. An apparatus as claimed in any one of claims 8 or 9 wherein one of the vessels contains a modifier along with the fluid and a restrictor is connected to an outlet of said vessel that contains the modifier.

* * * * *